United States Patent [19]
Hutton

[11] Patent Number: 5,929,242
[45] Date of Patent: Jul. 27, 1999

[54] MANUFACTURE OF LEVOBUPIVACAINE AND ANALOGUES THEREOF FROM L-LYSINE

[75] Inventor: Gordon Eric Hutton, Cambridge, United Kingdom

[73] Assignee: Darwin Discovery Limited, United Kingdom

[21] Appl. No.: 08/817,460

[22] PCT Filed: Oct. 9, 1995

[86] PCT No.: PCT/GB95/02385

§ 371 Date: Jun. 9, 1997

§ 102(e) Date: Jun. 9, 1997

[87] PCT Pub. No.: WO96/11181

PCT Pub. Date: Apr. 18, 1996

[30] Foreign Application Priority Data

Oct. 7, 1994 [GB] United Kingdom ............. 9420243
Mar. 10, 1995 [GB] United Kingdom ............. 9504928

[51] Int. Cl.⁶ .................. C07D 211/02; C07D 211/30
[52] U.S. Cl. .......................... 546/225; 514/330; 564/194
[58] Field of Search .................. 564/194; 546/225; 514/330

[56] References Cited

PUBLICATIONS

Kisfaludy et al, Synthesis, p. 163, 1982.

Kedger et al, Australina Journal of Chemistry, vol. 18, pp. 933–935, 1965.

*Primary Examiner*—Shailendra Kumar
*Attorney, Agent, or Firm*—Saliwanchik, Lloyd & Saliwanchik

[57] ABSTRACT

The subject invention concerns a compound of formula (X),

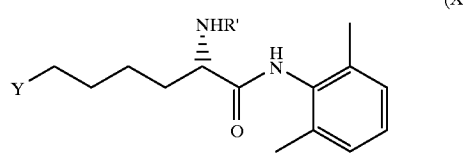

which can be prepared from the starting material L-lysine, and converted to levobupivacaine by cyclization.

28 Claims, No Drawings

MANUFACTURE OF LEVOBUPIVACAINE AND ANALOGUES THEREOF FROM L-LYSINE

This application is a 371, filed Oct. 9, 1995.

FIELD OF THE INVENTION

This invention relates to a cost-effective process for the conversion, via diazotisation methodology, of L-lysine to a carboxanilide precursor of levobupivacaine and related compounds.

BACKGROUND OF THE INVENTION

Compounds of formula 1 wherein R is a methyl, n-propyl or n-butyl group are widely used as local anaesthetics. Biological studies have shown that the (S)-enantiomers of such compounds (e.g. levobupivacaine wherein R is n-butyl) display lower cardiotoxicity than the corresponding racemates whilst maintaining the same anaesthetic potency, and are therefore more beneficial for clinical uses. Thus there is a requirement for efficient processes to manufacture compounds of formula 1 in the form of single enantiomers. The process embodied by the present invention employs a chirality pool approach to levobupivacaine, commencing from L-lysine, an inexpensive starting material which is readily available in bulk.

Although L-lysine has been converted through to optically enriched L-pipecolic acid and esters thereof by diazotisation and cyclisation reactions, cyclisation of an intermediate to form a piperidine-2-carboxanilide directly has hitherto not been reported. Furthermore, in the context of the present invention, these existing methods are hampered by an excessive number of steps required for manipulation of protecting groups in order to obviate Walden inversion at the carboxyl-bearing centre, which leads to the formation of D-pipecolic acid.

An additional benefit of the invention is the provision of unnatural amino acids of formula 2 with (S) configuration, which are important as pharmaceutical intermediates, e.g. for incorporation into physiologically active synthetic peptides. Compound 2a is commonly prepared by a multistep synthesis of the racemate commencing from dihydropyran followed by enzymatic resolution of an ester derivative (e.g. p-nitrobenzyl). This process in inefficient with respect to the number of steps required and by the fact that resolution produces up to 50% of an unwanted enantiomer. Diazotisation of L-lysine and derivatives thereof has been identified as an alternative strategy for the preparation of 2-amino-6-hydroxyhexanoic acid and derivatives thereof. However, such an approach has hitherto only been applied to the synthesis of compound 2c, but this process, employing sodium nitroprusside, is low yielding (28%).

Copper complexation of lysine and similar amino-acids has been extensively used as a technique for temporary protection of the α-amino acid moiety, as disclosed by Ledger et al, Anstr. J. Chem. 18:933–5 (1965). This procedure facilitates selective transformation of the second amino group present in the side-chain, e.g. the attachment of a covalently-bonded amino-protecting group.

SUMMARY OF THE INVENTION

This invention provdes a cost-effective process for preparing compounds of formula 1, wherein R is H or alkyl, from the inexpensive starting material L-lysine, using a chirality pool approach, and involving scission of the terminal C—N bond of L-lysine. In particular, the present invention provides a practical and economical process for the manufacture of levobupivacaine from L-lysine, which is exemplified in Scheme 1. This process involves the preparation of novel compounds of formula (X) as defined in claim 1; either R' is a protecting group, in which case R is H in the product, which can then be alkylated as desired, or R' is alkyl and corresponds to R as alkyl.

DESCRIPTION OF THE INVENTION

Formula (X), and other formulae used herein, refer to compounds that have at least predominantly the given stereochemistry. They are at least substantially free of their optical antipode, e.g. in at least 50%, more preferably at least 70% or 99%, enantiomeric excess.

According to the particular reactions shown in Scheme 1, the α-N-benzyloxycarbonyl derivative of L-lysine is initially (a) subjected to diazotisation in the presence of acetic acid to afford (S)-2-(benzyloxycarbonylamino)-6-acetoxyhexanoic acid (2b). Alternatively, Z may be any other blocking group, many examples of which are well known to the skilled man.

The next three steps of Scheme 1 proceed by way of novel compounds 3–5: (b) Condensation with 2,6-dimethylaniline gives compound 3; (c) cleavage of the 0-acetyl group by methanolysis gives compound 4; and (d) tosylation gives compound 5. The OTs group shown in Scheme 1 is merely one example of many leaving groups which can be used and which are known to the skilled man. Examples are given in claim 2.

Finally, compound 5 is (a) subjected to hydrogenation in the presence of base to effect direct conversion to enantiomerically pure (S)2',6'-dimethylpiperidine-2-carboxanilide 6. Variants of this process include conversion of the α-N-benzyloxycarbonyl (or other blocked) derivative of L-lysine to compound 6 via alkyl halide derivatives of formula 7. The conversion of compound 6 to levobupivacaine or other N-alkylated analogues can be carried out by methodology known to those skilled in the art, or as described in another Patent Application filed today, claiming priority from British Patent Application No. 9421478.0. Preferably, R is methyl, n-propyl, cyclopropyl or, most preferably, n-butyl.

A preferred aspect of the process summarised in Scheme 1 is the use of either sodium nitrite/sodium acetate/acetic acid or isoamyl nitrite/acetic acid as efficient reagent systems for the conversion of α-N-benzyloxycarbonyl or otherwise blocked L-lysine to the compound 2b, by formation of a diazonium intermediate followed by solvolysis of this species or of the carbocation formed by loss of $N_2$. This discovery provides significant benefit over the prior art process since the yields are much higher (60–87% of 2b compared to 28% 2c).

As a further feature of the invention, we have discovered that L-lysine can be cleanly and efficiently converted to (S)-2-amino-6-hydroxyhexanoic acid 2a in a process (Scheme 2) involving sequential formation of bis(lysinato) copper, diazotisation-solvolysis to generate the novel copper (II) complex 8, and cation-exchange to effect decomplexation. Diazotisation-solvolysis in such processes can be effected in aqueous media using either sodium nitroprusside at pH>10 or sodium nitrite, e.g. at pH<4.

More generally, $NH_2$ may be converted to any leaving group Y, e.g. halide, usually under anhydrous conditions, using known methodology. Depending on the stability of the metal complex, the reaction proceeds in one or more steps, to give a compound of the formula $$Y-(CH_2)_4-CH(NH_2)-COOH$$

in optically-enriched form. The free amine may be blocked at this stage, as a reactant for use in Scheme 1.

Such processes are advantageous over conventional diazotisations of L-lysine, which give mixtures of products arising from unselective transformation of either one, and in some cases both, of the two amine groups present.

The following Examples illustrate the invention. Examples 1 to 5 illustrate respective steps in Scheme 1; Example 6 illustrates Scheme 2.

EXAMPLE 1

A stirred solution of $N^\alpha$-benzyloxycarbonyl L-lysine (6.33 g, 22.6 mmol) in acetic acid (150 ml) was treated with sodium acetate (1.85 g) and then sodium nitrite (1.56 g×3) at 40° C. The reaction was stirred for 3 hours at 40° C., cooled and the bulk of the acetic acid was removed in vacuo and the residues partitioned between water (100 ml) and dichloromethane (100 ml×3). The combined organic extracts were dried ($MgSO_4$) and evaporated in vacuo to give compound 2b a yellow oil (6.35 g, 87%).

EXAMPLE 2

Isoamyl nitrite (6.1 ml) was added to a stirred solution of $N^\alpha$-benzyloxycarbonyl L-lysine (6.34 g, 22.6 mmol) in glacial acetic acid (35 ml) at 22° C. The mixture was heated at 50° C. for 12 hours, then volatile material removed by distillation in vacuo (last traces removed via formation of azeotopic mixtures with toluene) to give compound 2b (4.38 g, 60%).

EXAMPLE 3

A solution of compound 2b (6.35g, 19.7 mmol) in dichloromethane (150 ml) was treated sequentially with 2,6-dimethylaniline and a solution of dicyclohexylcarbodiimide (4.89 g) in dichloromethane (10 ml) at 18° C. The reaction was stirred for 24 hours. The precipitate which formed was filtered and washed with dichloromethane (100 ml). The organics were concentrated in vacuo to give compound 3 as waxy solid. Without further treatment, this material was dissolved in MeOH (150 ml) and solid $K_2CO_3$ (9.57 g) was added. The reaction was stirred for 24 hours then filtered and evaporated to leave a waxy solid which was chromatographed on silica gel with 1.5:1 EtOAc:heptane to give compound 4 as a colourless solid (2.22 g, 28%).

EXAMPLE 4 p-Toluenesulphonyl chloride (0.4 g) was added to a solution of compound 4 (0.60 g, 1.7 mmol) and pyridine (1.4 ml) in dichloromethane (5 ml) and stirred for 4 hours. Dilute hydrochloric acid (1 N; 10 ml) was added, and after stirring for 18 hours the mixture was extracted with dichloromethane (50 ml). The organic solution was washed with aqueous NaOH (1 N; 10 ml), dried ($MgSO_4$) and evaporated in vacuo to give a yellow oil which was chromatographed on silica gel eluting with 1:1 EtOAc:heptane. This gave compound 5 as a colourless oil (0.76 g, 81%) which slowly solidifies as the tosyl derivative.

EXAMPLE 5

A mixture of compound 5 (0.76 g, 1.4 mmol), Pd/C (0.076 g) and $K_2CO_3$ (0.47 g) in EtOH (15 ml) was placed under an atmosphere of hydrogen (balloon) and stirred vigourously for 3 hours. The reaction was filtered and the solids thoroughly washed with EtOH (5 ml). The combined filtrate and washings were concentrated in vacuo and the residue partitioned between dichloromethane (3×25 ml) and aqueous NaOH (1 N; 25 ml). The combined organic extracts were dried ($MgSO_4$) and concentrated in vacuo to give (S)-2',6'-dimethylpiperidine-2-carboxanilide 6 as a colourless solid (0.284g, 87%), which was shown by chiral HPLC analysis to have an optical purity of >98%.

EXAMPLE 6

A suspension of L-lysine (0.931 g, 5.1 mmol) and $CuCO_3.Cu(OH)_2$ (1.24 g, 5.6 mmol) in water (15 ml) was heated under reflux for 5 minutes then cooled and filtered. The pH of the filtrate was adjusted to 4 with 2M $H_2SO_4$. A solution of sodium nitrite (0.70 g, 10 mmol) in water (5 ml) was added dropwise over 10 minutes and the mixture was stirred at 24° C. for 6 hours. Chelex 100 resin (40 g) was added to effect decomplexation. The resulting suspension was then filtered to give a solution of L-lysine (60%) and (S)-2-amino-6-hydroxyhexanoic acid 2 (30%).

(1)

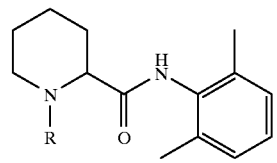

(2)

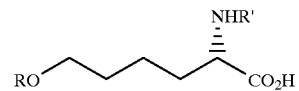

2a: R = R' = H
2b: R = Ac; R' = Z
2c: R = H, R' = Z

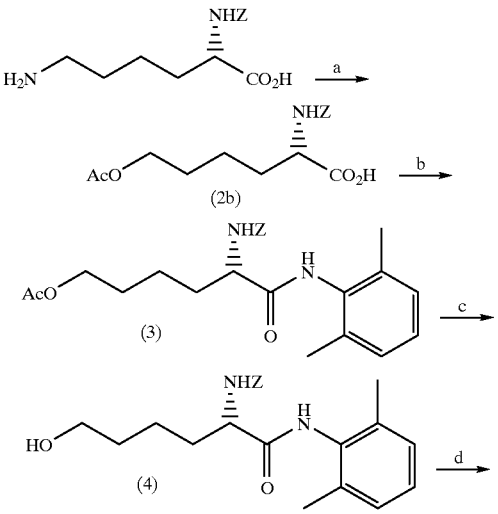

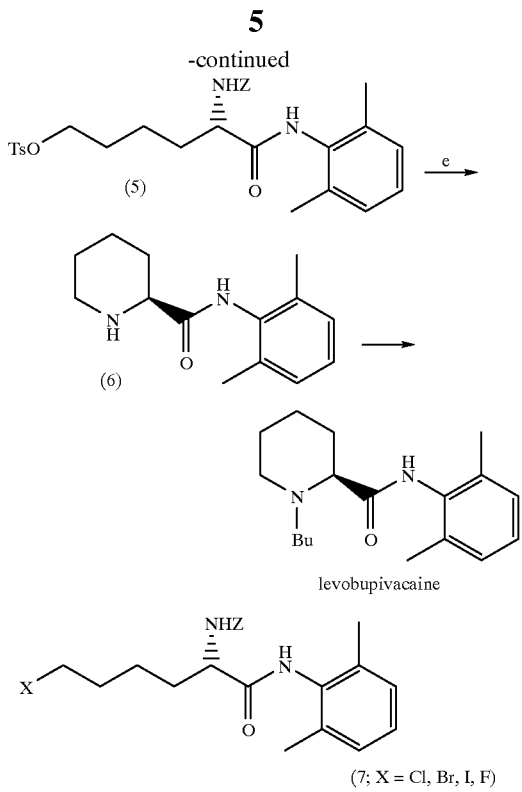

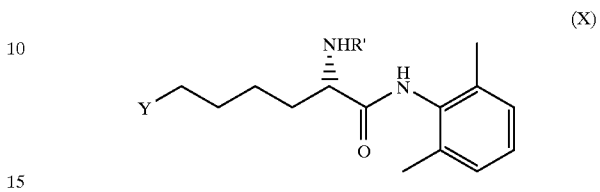

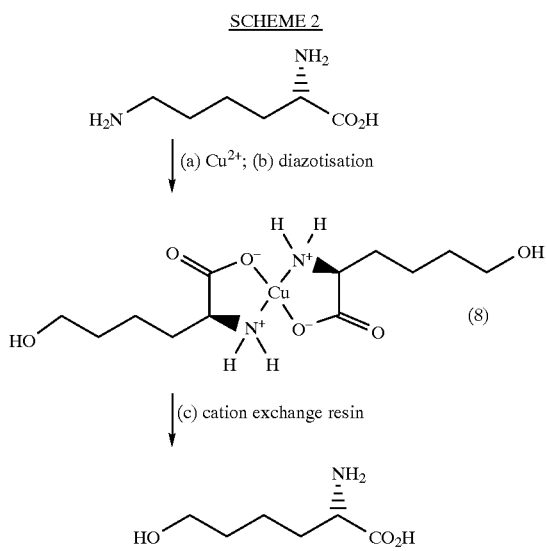

I claim:

1. A process for the manufacture of levobupivacaine, wherein said process comprises reaction of a compound of formula (X),

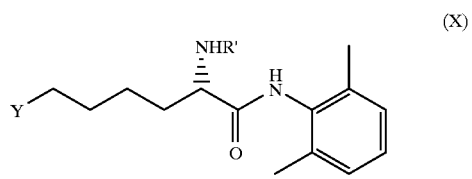

wherein R' is butyl or a removable amino-protecting group, under conditions whereby the NHR' group cyclises to the $CH_2Y$ group, with loss of the leaving group Y; and, if R' is an N-protecting group, N-butylation of the cyclised product.

2. A process for the manufacture of ropivacaine, wherein said process comprises reaction of a compound of formula (X), (X)

wherein R' is propyl, or a removable amino protecting group, under conditions whereby the NHR' group cyclises to the $CH_2Y$ group, with loss of the leaving group Y; and, if R' is an N-protecting group, N-propylation of the cyclised product.

3. The process according to claim 1, wherein said conditions comprise hydrogenation in the presence of base.

4. The process according to claim 1, which additionally comprises the prior steps of diazotisation-solvolysis of α-N-blocked-L-lysine; condensation of the resultant (S)-2-(blocked amino)-6-acetoxyhexanoic acid with 2,6-dimethylaniline; cleavage of the o-acetyl group, by methanolysis; and introducing the group Y into the resultant compound, to give the compound (X).

5. The process according to claim 1, which additionally comprises the prior steps of reacting L-lysine with $Cu^{2+}$ ion; subjecting the resultant complex to diazotisation-solvolysis; cation-exchange to effect decomplexation; condensation of the resultant (S)-2-amino-6-hydrohexanoic acid with 2,6-dimethylaniline; and introducing the group Y and the blocking group R' into the resultant compound, to give the compound (X).

6. The process according to claim 2, wherein said conditions comprise hydrogenation in the presence of base.

7. The process according to claim 2, which additionally comprises the prior steps of diazotisation-solvolysis of α-N-blocked-L-lysine; condensation of the resultant (S)-2-(blocked amino)-6-acetoxyhexanoic acid with 2,6-dimethylaniline; cleavage of the o-acetyl group, by methanolysis; and introducing the group Y into the resultant compound, to give the compound (X).

8. The process according to claim 2, which additionally comprises the prior steps of reacting L-lysine with $Cu^{2+}$ ion; subjecting the resultant complex to diazotisation-solvolysis; cation-exchange to effect decomplexation; condensation of the resultant (S)-2-amino-6-hydrohexanoic acid with 2,6-dimethylaniline; and introducing the group Y and the blocking group R' into the resultant compound, to give the compound (X).

9. The process according to claim 1, wherein R' of formula (X) is an amino-protecting group.

10. The process according to claim 1, wherein Y of formula (X) is selected from the group consisting of $N_2$, OH, O-acyl, O-alkylsulphonyl, O-arylsulphonyl and halide.

11. The process according to claim 1, wherein R' of formula (X) is benzyloxycarbonyl.

12. The process according to claim 1, wherein Y is p-toluenesulphonyloxy.

13. The process according to claim 5, wherein diazotisation-solvolysis is effected using sodium nitroprusside at basic pH.

14. The process according to claim 5, wherein diazotisation-solvolysis is effected using sodium nitrite at acidic pH.

15. The process according to claim 13, wherein said pH is above about 10.

16. The process according to claim 14, wherein said pH is below about 5.

17. The process according to claim 8, wherein diazotisation-solvolysis is effected using sodium nitroprusside at basic pH.

18. The process according to claim 8, wherein diazotisation-solvolysis is effected using sodium nitrite at acidic pH.

19. The process according to claim 17, wherein said pH is above about 10.

20. The process according to claim 18, wherein said pH is below about 5.

21. The process, according to claim 4, wherein the diazotisation/solvolysis comprises using sodium nitrite and sodium acetate in acetic acid.

22. The process according to claim 4, wherein the diazotisation/solvolysis comprises using isoamyl nitrite in acetic acid.

23. The process according to claim 7, wherein the diazotisation/solvolysis comprises using sodium nitrite and sodium acetate in acetic acid.

24. The process according to claim 7, wherein the diazotisation/solvolysis comprises using isoamyl nitrite in acetic acid.

25. The process according to claim 2, wherein R' of formula (X) is an amino-protecting group.

26. The process according to claim 2, wherein Y of formula (X) is selected from the group consisting of $N_2$, OH, O-acyl, O-alkylsulphonyl, O-arylsulphonyl and halide.

27. The process according to claim 2, wherein R' of formula (X) is benzyloxycarbonyl.

28. The process according to claim 27, wherein Y is p-toluenesulphonyloxy.

\* \* \* \* \*

UNITED STATES PATENT AND TRADEMARK OFFICE
CERTIFICATE OF CORRECTION

PATENT NO. : 5,929,242
DATED : July 27, 1999
INVENTOR(S) : Gordon Eric Hutton

It is certified that error appears in the above-identified patent and that said Letters Patent is hereby corrected as shown below:

Column 8,
Line 13, "OII" should read -- OH --.

Signed and Sealed this

Twelfth Day of March, 2002

Attest:

Attesting Officer

JAMES E. ROGAN
Director of the United States Patent and Trademark Office